US011833279B2

(12) United States Patent
Lutz et al.

(10) Patent No.: US 11,833,279 B2
(45) Date of Patent: Dec. 5, 2023

(54) SYSTEM AND METHOD FOR ISOLATING ALPHA 2M MOLECULES

(71) Applicant: Astaria Global, LLC, Houston, TX (US)

(72) Inventors: David J. Lutz, Pipe Creek, TX (US); William J. Cramer, Houston, TX (US); Michael D. Duvall, Houston, TX (US); Robert S. Shoemaker, Eagle, ID (US)

(73) Assignee: ASTARIA GLOBAL, LLC, Houston, TX (US)

( * ) Notice: Subject to any disclaimer, the term of this patent is extended or adjusted under 35 U.S.C. 154(b) by 0 days.

(21) Appl. No.: 17/837,090

(22) Filed: Jun. 10, 2022

(65) Prior Publication Data

US 2022/0395624 A1    Dec. 15, 2022

Related U.S. Application Data

(63) Continuation of application No. 63/209,685, filed on Jun. 11, 2021.

(51) Int. Cl.
*A61M 1/02*  (2006.01)
*B01L 3/00*  (2006.01)
(Continued)

(52) U.S. Cl.
CPC .............. *A61M 1/029* (2013.01); *A61J 1/201* (2015.05); *A61J 1/2062* (2015.05); *A61J 1/2082* (2015.05);
(Continued)

(58) Field of Classification Search
CPC ............ A61M 1/029; A61M 2202/0417; A61J 1/201; A61J 1/2062; A61J 1/2082;
(Continued)

(56) References Cited

U.S. PATENT DOCUMENTS 3,300,051 A * 1/1967 Mitchell ................. B01L 3/569
422/918
3,610,241 A * 10/1971 LeMarie ............. A61M 5/1782
604/407

(Continued)

FOREIGN PATENT DOCUMENTS

| CN | 101992136 B | 9/2012 |
| CN | 109206506 A | 1/2019 |
| WO | 2013126587 A1 | 8/2013 |

OTHER PUBLICATIONS

Lenntech Molecular weight cutoff https://www.lenntech.com/services/mwco.htm (Year: 1998).*

(Continued)

*Primary Examiner* — Liam Royce
(74) *Attorney, Agent, or Firm* — The Juhasz Law Firm

(57) ABSTRACT

A method includes: depositing whole blood into at least one separator tube; subjecting the at least one separator tube to a first centrifugal force to cause a combination of the first centrifugal force and separator gel within each separator tube of the at least one separator tube to separate plasma of the whole blood from red and white blood cells of the whole blood within the at least one separator tube, wherein the plasma includes α2M molecules; transferring one or more portions of the plasma from within the at least one separator tube and into at least one isolator; and subjecting the at least one isolator to a second centrifugal force to cause a combination of the second centrifugal force and a filter within each isolator of the at least one isolator to isolate the α2M molecules from other components of the plasma within the at least one isolator.

17 Claims, 12 Drawing Sheets

(51) Int. Cl.
  *A61K 35/16* (2015.01)
  *A61J 1/20* (2006.01)
  *A61K 38/17* (2006.01)
  *A61K 38/57* (2006.01)

(52) U.S. Cl.
  CPC ............. *A61J 1/2096* (2013.01); *A61K 35/16* (2013.01); *A61K 38/1722* (2013.01); *A61K 38/57* (2013.01); *B01L 3/5021* (2013.01); *B01L 3/50825* (2013.01); *A61M 2202/0417* (2013.01); *B01L 2300/0832* (2013.01); *B01L 2400/0409* (2013.01); *B01L 2400/0478* (2013.01)

(58) Field of Classification Search
  CPC ... A61J 1/2096; A61K 35/16; A61K 38/1722; A61K 38/57; B01L 3/5021; B01L 3/50825; B01L 2300/0832; B01L 2400/0409; B01L 2400/0478
  See application file for complete search history.

(56) References Cited

U.S. PATENT DOCUMENTS

| | | | |
|---|---|---|---|
| 3,939,822 A * | 2/1976 | Markowitz | B01L 3/5021 604/190 |
| 4,957,637 A * | 9/1990 | Cornell | A61B 5/150389 422/550 |
| 5,599,558 A * | 2/1997 | Gordinier | A61K 35/16 530/382 |
| 6,471,069 B2 | 10/2002 | Lin et al. | |
| 8,540,082 B2 | 9/2013 | Kelland et al. | |
| 9,352,021 B2 | 5/2016 | Hanna et al. | |
| 9,498,514 B2 | 11/2016 | Hanna et al. | |
| 10,265,388 B2 | 4/2019 | Hanna et al. | |
| 10,400,028 B2 | 9/2019 | Hanna et al. | |
| 10,518,275 B2 | 12/2019 | Sengun et al. | |
| 10,940,189 B2 | 3/2021 | Hanna et al. | |
| 11,040,092 B2 | 6/2021 | Hanna et al. | |
| 2001/0016703 A1* | 8/2001 | Wironen | B01F 35/71 604/82 |
| 2007/0102344 A1 | 5/2007 | Konrad | |
| 2009/0078638 A1* | 3/2009 | Bonhomme | B01L 3/5021 210/348 |
| 2014/0360944 A1* | 12/2014 | Esteron | A61M 1/3693 210/698 |
| 2018/0093270 A1* | 4/2018 | Ladtkow | G01N 35/00069 |
| 2018/0296748 A1* | 10/2018 | Emerson | A61J 1/2013 |
| 2020/0305781 A1* | 10/2020 | Aljefri | B04B 5/0428 |

OTHER PUBLICATIONS

Linquip 2020 "Centrifuge rotor types: an insight to the types, uses and the history". linquip.com/blog/centrifuge-rotor-types-uses-and-the-history/ (Year: 2020).*
International Search Report of PCT/US2022/032960. (Year: None).*
Written Opinion of the International Searching Authority of PCT/US2022/032960. (Year: None).*

* cited by examiner

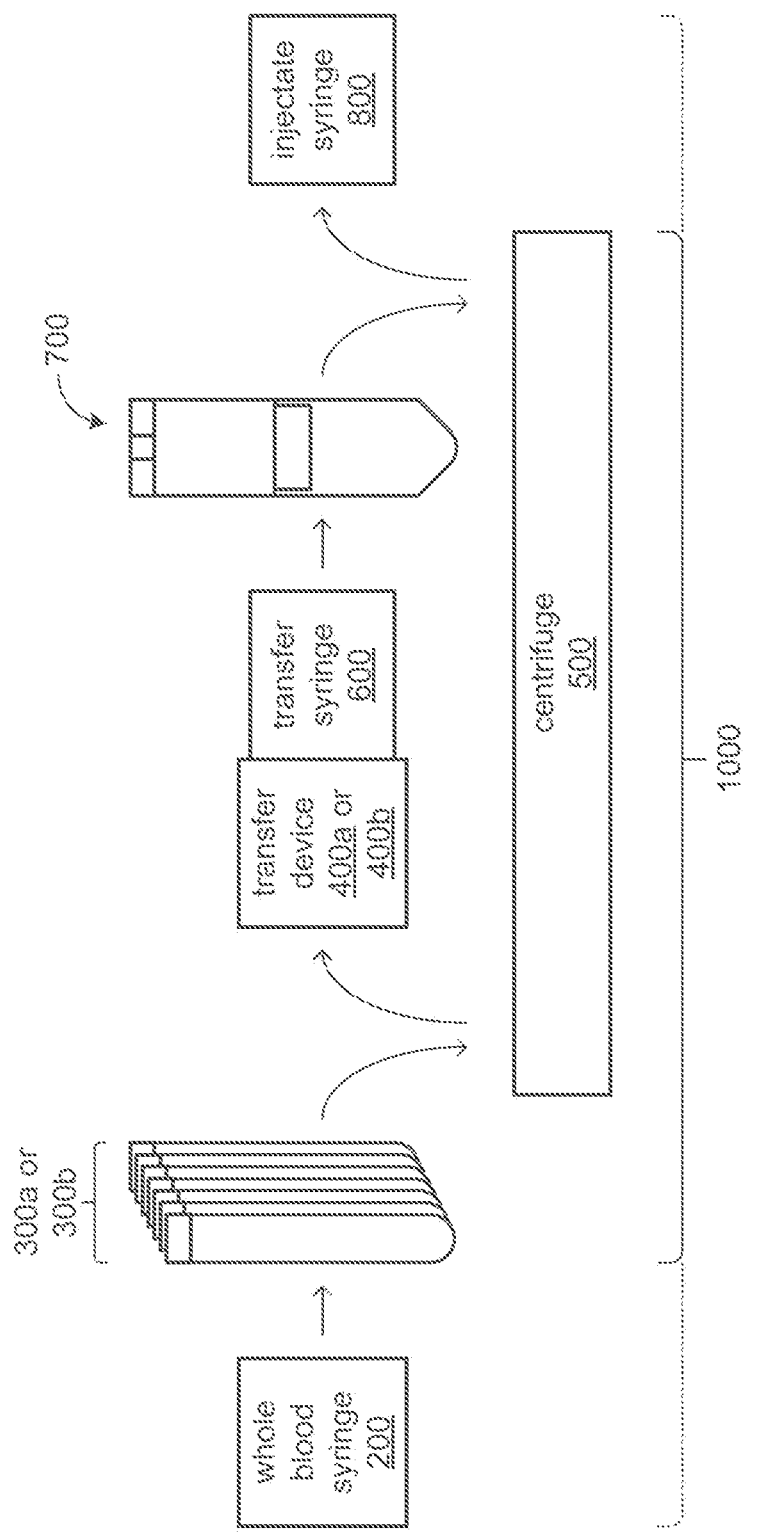

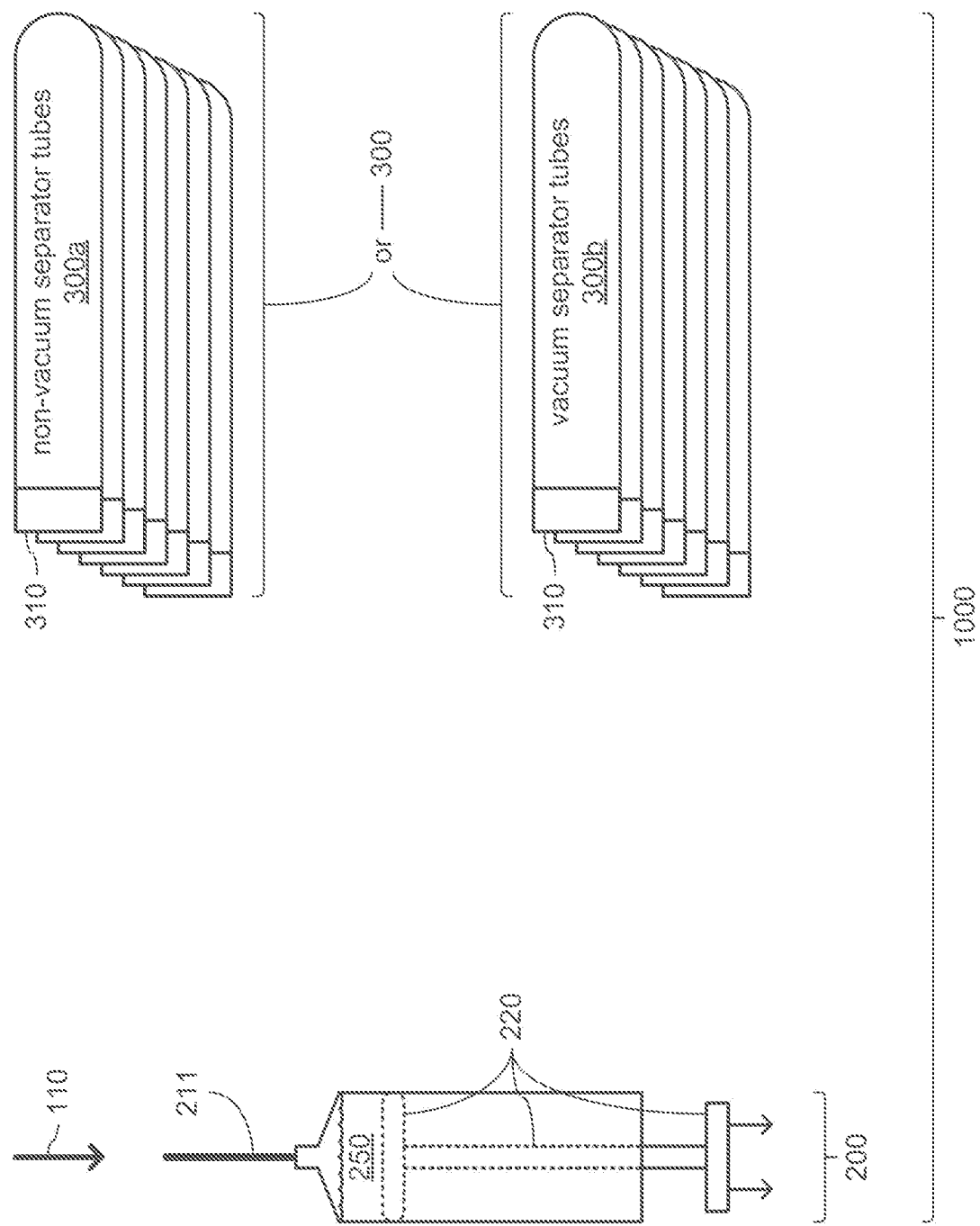

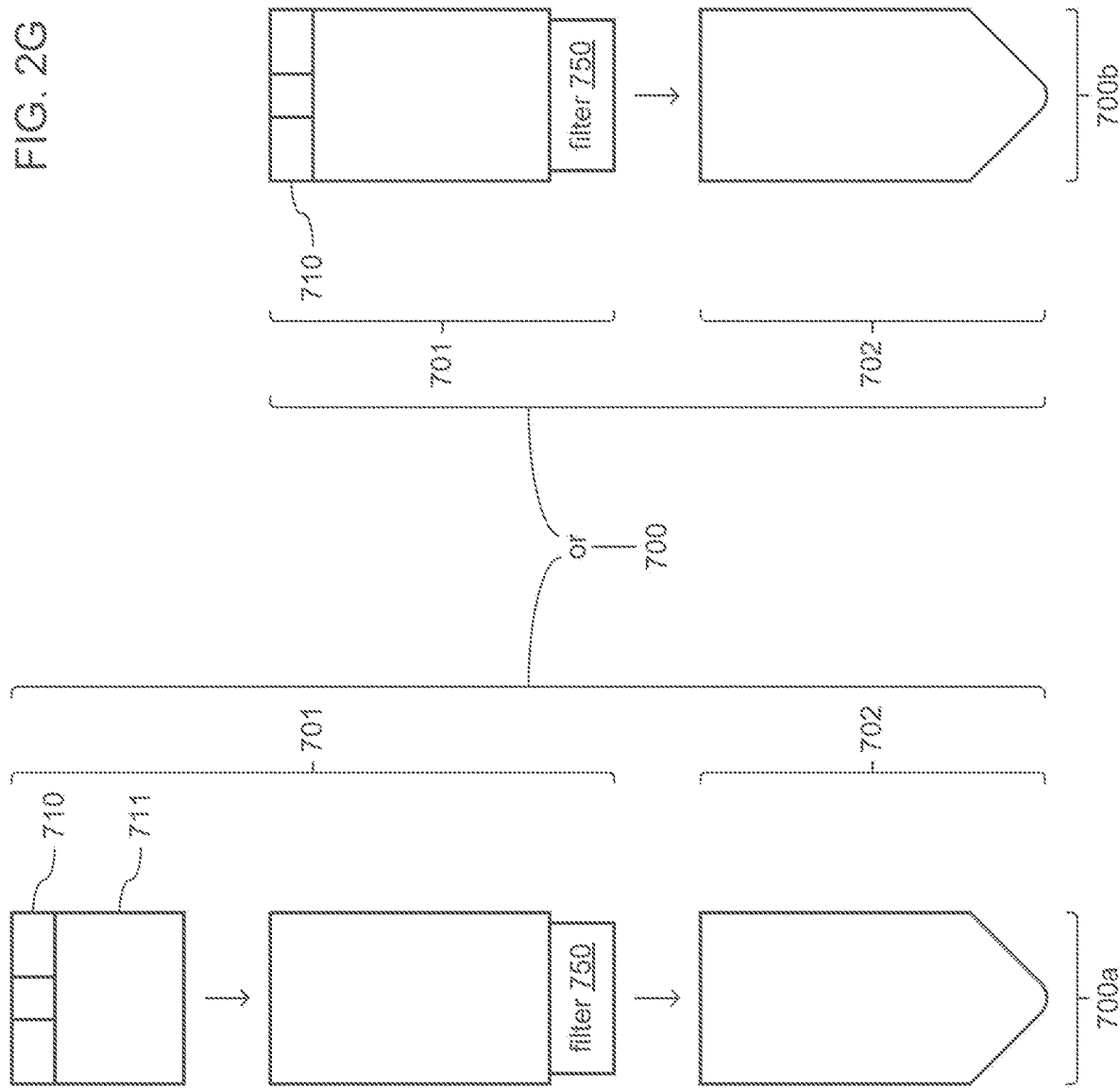

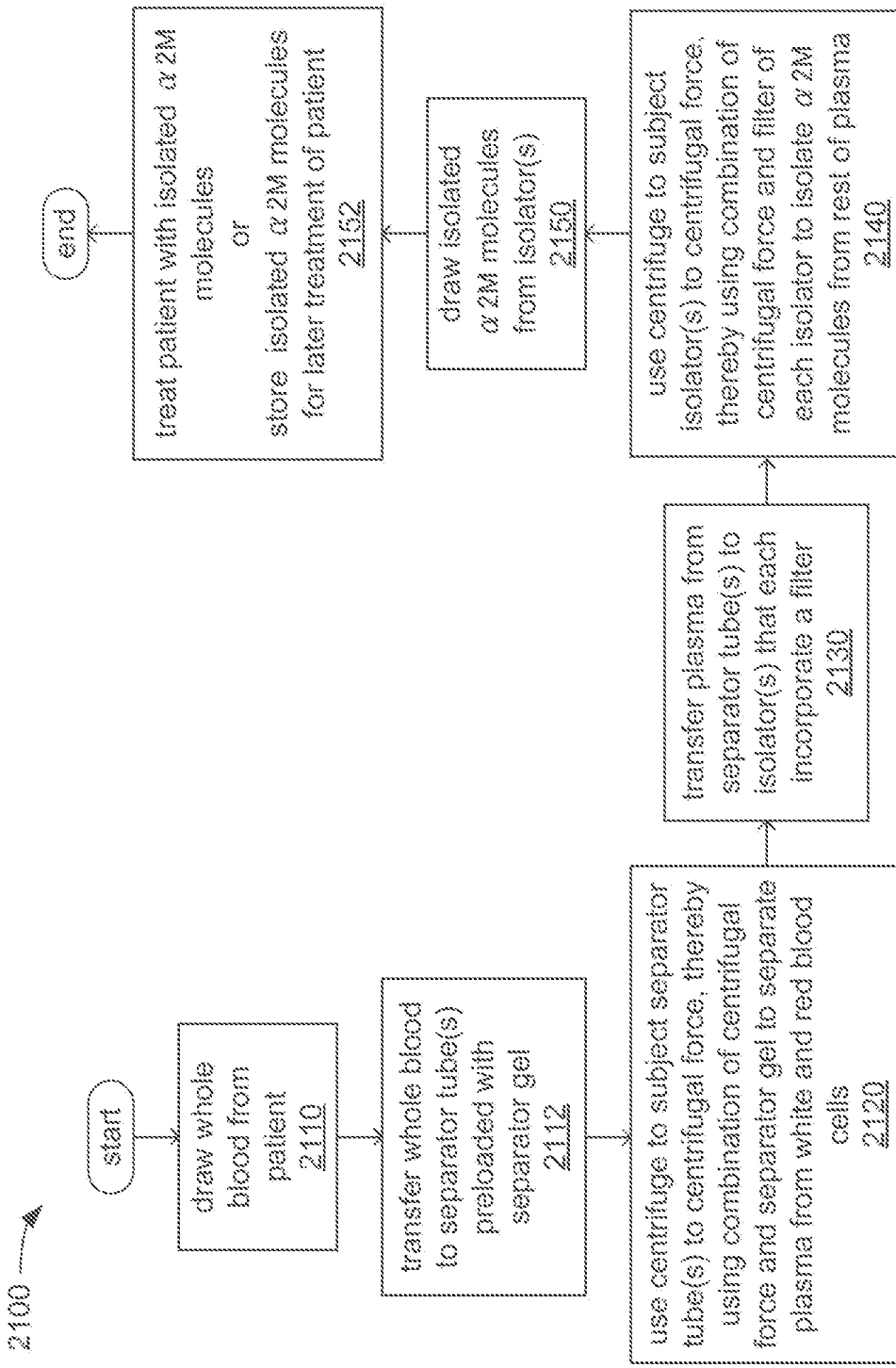

SYSTEM AND METHOD FOR ISOLATING ALPHA 2M MOLECULES

RELATED APPLICATION

This application claims the benefit of the priority date of U.S. Provisional Application 63/209,685 filed Jun. 11, 2021, the disclosure of which his also incorporated herein by reference for all purposes.

BACKGROUND

1. Technical Field

The present disclosure relates to medical procedures for the isolation and delivery of Alpha-2 Macroglobulin (α2M) molecules from a patient's own blood plasma to treat musculoskeletal conditions.

2. Description of the Related Art

Platelet-rich plasma (PRP) and platelet-poor plasma (PPP) therapies have become accepted forms of treatment for various musculoskeletal conditions. In PRP and PPP therapies, components of a patient's own blood are isolated and then injected into affected areas of the patient's body to accelerate the healing of injured musculoskeletal components such as tendons, ligaments, muscles and joints. As will be familiar to those skilled in the art, such therapies require the use of blood components (e.g., Alpha-2 Macroglobulin molecules) from the blood of the specific patient that is being treated such that those blood components are said to represent autologous ortho-biologics. Thus, PRP and PPP therapies make use of a patient's own healing system to address musculoskeletal conditions.

In one form of both PRP and PPP therapies, the treatment of joints includes the injection of Alpha-2 Macroglobulin (α2M) molecules isolated from the plasma of the patient's own blood. More specifically, the injection of α2M molecules into a patient's joint may be employed to slow the progression of a degenerative joint disease (e.g., osteoarthritis) by preventing (or at least arresting) the breakdown and loss of cartilage therein.

Unfortunately, the isolation of α2M molecules for such an injection is a laborious and time-consuming process requiring specialized expensive equipment that is normally available only in a laboratory. Among such specialized expensive equipment is a peristaltic pump. While hospitals and/or other relatively large medical facilities may have such equipment and available personnel to carry out such an isolation process, smaller medical facilities (e.g., the doctor offices often located in rural areas) often do not.

Additionally, even where such a smaller medical facility is able to acquire such specialized expensive equipment and/or has the necessary personnel available for such a laborious and time-consuming process, there may be situations in which bringing a patient to such a medical facility may be prohibitively difficult, if not impossible, thereby necessitating making house calls. Such situations may arise, for example, in the case of human patients with severe limitations in their mobility. Such situations may also arise, for example, in the case of equine patients and/or other large four-legged animal patients that may be at least difficult to transport.

The need to make house calls as part of treating patients with α2M molecules can result in considerable delays in the commencement of treatment due to the need to draw blood and then inject α2M molecules in separate visits, as a result of needing to bring the drawn blood back to the medical facility where such specialized expensive equipment is maintained. An effort could be made to reduce such delays by bringing such specialized expensive equipment to patient locations as part of making house calls, but this can result in damage to such equipment and/or in causing such equipment to become less available for use in helping other patients by not leaving it in place at a medical facility. Further, the performance of the laborious and time-consuming process of isolating α2M molecules during a house call can make the duration of a house call prohibitively long.

A need exists for a less time-consuming and cumbersome approach to isolating α2M molecules during a house call.

BRIEF SUMMARY

Technologies are described for more efficiently isolating α2M molecules in a non-laboratory setting for use in treating musculoskeletal conditions.

A method for isolating Alpha-2 Macroglobulin (α2M) molecules from whole blood includes: depositing whole blood into at least one separator tube, wherein each separator tube of the at least one separator tube contains an amount of separator gel; subjecting the at least one separator tube to a first centrifugal force in a first centrifuging stage for a first predetermined period of time to cause a combination of the first centrifugal force and the separator gel within each separator tube of the at least one separator tube to separate plasma of the whole blood within the at least one separator tube from red blood cells and white blood cells of the whole blood within the at least one separator tube, wherein the plasma includes the α2M molecules; transferring one or more portions of the plasma from within the at least one separator tube and into at least one isolator, wherein each isolator of the at least one isolator comprises a filter; and subjecting the at least one isolator to a second centrifugal force in a second centrifuging stage for a second predetermined period of time to cause a combination of the second centrifugal force and the filter within each isolator of the at least one isolator to isolate the α2M molecules from other components of the plasma within the at least one isolator.

A kit for isolating Alpha-2 Macroglobulin (α2M) molecules from whole blood includes at least one separator tube, wherein: each separator tube of the at least one separator tube comprises an elongate transparent tube that defines an opening at one end that is sealed with a cap; each separator tube of the at least one separator tube contains an amount of separator gel; the cap is formed from a flexible material that allows a hollow needle of a transfer syringe to penetrate therethrough while sealing around the hollow needle, and that re-seals after the hollow needle is withdrawn; and the kit is available in multiple versions that are differentiated by at least a quantity of separator tubes that are included. The kit also includes at least one isolator, wherein: each isolator of the at least one isolator comprises a first cylinder defined by a first cylindrical wall and a second cylinder defined by a second cylindrical wall; each isolator of the at least one isolator comprises a filter; a first end of the first cylindrical wall of the first cylinder defines an opening that is configured to be closable with a septum cap, and a second end of the first cylindrical wall is closed with the filter; a first end of the second cylindrical wall of the second cylinder is closed where the second cylindrical wall narrows to form a conically-shaped end portion, and the second end of the second cylindrical wall of the second cylinder defines an opening that is configured to be coupled to the second end of the first cylinder in a manner that causes a first interior space of the first cylinder and a second interior space of the second cylinder to be separated by the filter; and at least a portion of the septum cap is formed from a flexible material that allows the hollow needle of the transfer syringe to penetrate therethrough while sealing around the hollow needle, and that re-seals after the hollow needle is withdrawn. The kit further includes a centrifuge that is configured to: subject the at least one separator tube to a first centrifugal force in a first centrifuging stage for a first predetermined period of time to cause a combination of the first centrifugal force and the separator gel within each separator tube of the at least one separator tube to separate plasma of the whole blood within the at least one separator tube from red blood cells and white blood cells of the whole blood within the at least one separator tube, wherein the plasma includes the α2M molecules; and subject the at least one isolator to a second centrifugal force in a second centrifuging stage for a second predetermined period of time to cause a combination of the second centrifugal force and the filter within each isolator of the at least one isolator to isolate the α2M molecules from other components of the plasma within the at least one isolator. The additionally includes the transfer syringe, wherein, between the first centrifuging stage and the second centrifuging stage, the transfer syringe is configured to transfer the plasma from the at least one separator tube and into the at least one isolator by: being inserted through the cap of each separator tube of the at least one separator tube to withdraw the plasma from within the at least one separator tube; and being inserted through the septum cap of each isolator of the at least one isolator to inject the plasma into the at least one isolator.

BRIEF DESCRIPTION OF THE DRAWINGS

The disclosure will be better understood and when consideration is given to the drawings and the detailed description which follows. Such description makes reference to the annexed drawings wherein:

FIG. 1 is an overview block diagram of aspects of an example system and method of isolating α2M from whole blood in preparation for delivery by injection.

FIGS. 2a, 2b, 2c, 2d, 2e, 2f, 2g, 2h, 2i and 2j, together, provide a more detailed presentation of aspects of the example system and method of FIG. 1.

FIG. 3 provides a flow chart of the method of FIG. 1.

DETAILED DESCRIPTION

Figure 2B:
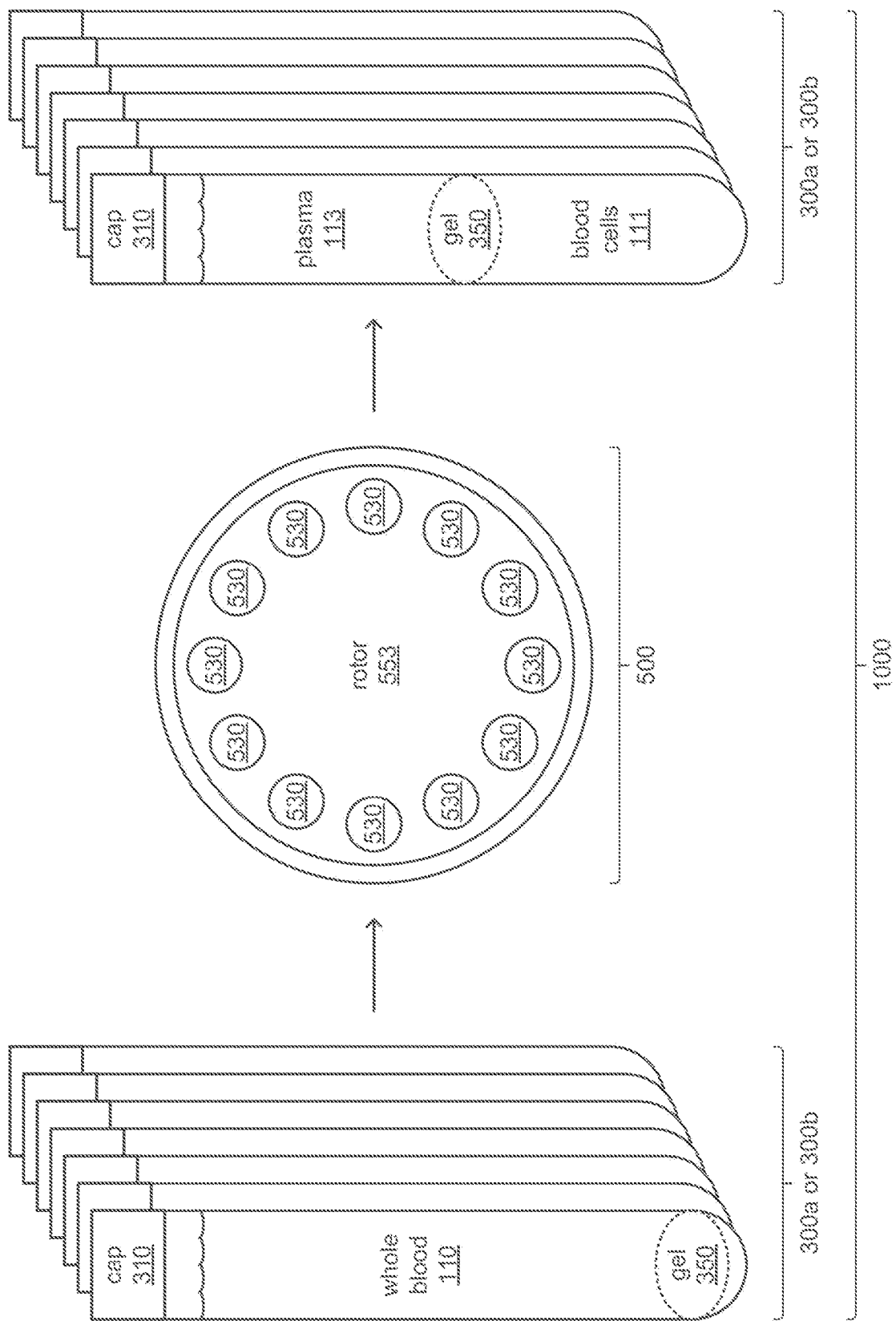

In the following detailed description, reference is made to the accompanying drawings that form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Disclosed herein is an α2M molecule isolation system implementing a method for isolating of α2M molecules from whole blood of a patient in preparation for use in treating a musculoskeletal condition of that patient.

A method for isolating Alpha-2 Macroglobulin (α2M) molecules from whole blood includes: depositing whole blood into at least one separator tube, wherein each separator tube of the at least one separator tube contains an amount of separator gel; subjecting the at least one separator tube to a first centrifugal force in a first centrifuging stage for a first predetermined period of time to cause a combination of the first centrifugal force and the separator gel within each separator tube of the at least one separator tube to separate plasma of the whole blood within the at least one separator tube from red blood cells and white blood cells of the whole blood within the at least one separator tube, wherein the plasma includes the α2M molecules; transferring one or more portions of the plasma from within the at least one separator tube and into at least one isolator, wherein each isolator of the at least one isolator comprises a filter; and subjecting the at least one isolator to a second centrifugal force in a second centrifuging stage for a second predetermined period of time to cause a combination of the second centrifugal force and the filter within each isolator of the at least one isolator to isolate the α2M molecules from other components of the plasma within the at least one isolator.

A kit for isolating Alpha-2 Macroglobulin (α2M) molecules from whole blood includes at least one separator tube, wherein: each separator tube of the at least one separator tube comprises an elongate transparent tube that defines an opening at one end that is sealed with a cap; each separator tube of the at least one separator tube contains an amount of separator gel; the cap is formed from a flexible material that allows a hollow needle of a transfer syringe to penetrate therethrough while sealing around the hollow needle, and that re-seals after the hollow needle is withdrawn; and the kit is available in multiple versions that are differentiated by at least a quantity of separator tubes that are included. The kit also includes at least one isolator, wherein: each isolator of the at least one isolator comprises a first cylinder defined by a first cylindrical wall and a second cylinder defined by a second cylindrical wall; each isolator of the at least one isolator comprises a filter; a first end of the first cylindrical wall of the first cylinder defines an opening that is configured to be closable with a septum cap, and a second end of the first cylindrical wall is closed with the filter; a first end of the second cylindrical wall of the second cylinder is closed where the second cylindrical wall narrows to form a conically-shaped end portion, and the second end of the second cylindrical wall of the second cylinder defines an opening that is configured to be coupled to the second end of the first cylinder in a manner that causes a first interior space of the first cylinder and a second interior space of the second cylinder to be separated by the filter; and at least a portion of the septum cap is formed from a flexible material that allows the hollow needle of the transfer syringe to penetrate therethrough while sealing around the hollow needle, and that re-seals after the hollow needle is withdrawn. The kit further includes a centrifuge that is configured to: subject the at least one separator tube to a first centrifugal force in a first centrifuging stage for a first predetermined period of time to cause a combination of the first centrifugal force and the separator gel within each separator tube of the at least one separator tube to separate plasma of the whole blood within the at least one separator tube from red blood cells and white blood cells of the whole blood within the at least one separator tube, wherein the plasma includes the α2M molecules; and subject the at least one isolator to a second centrifugal force in a second centrifuging stage for a second predetermined period of time to cause a combination of the second centrifugal force and the filter within each isolator of the at least one isolator to isolate the α2M molecules from other components of the plasma within the at least one isolator. The additionally includes the transfer syringe, wherein, between the first centrifuging stage and the second centrifuging stage, the transfer syringe is configured to transfer the plasma from the at least one separator tube and into the at least one isolator by: being inserted through the cap of each separator tube of the at least one separator tube to withdraw the plasma from within the at least one separator tube; and being inserted through the septum cap of each isolator of the at least one isolator to inject the plasma into the at least one isolator.

Turning to FIG. 1, an α2M molecule isolation system 1000 may include one or more of a whole blood syringe 200, a set of multiple separator tubes 300, a transfer device 400, a centrifuge 500, a transfer syringe 600, one or more isolators 700, and/or an injectate syringe 800. Thus the system 1000 may be implemented as a kit that is made up of a relatively small number of relatively small and lightweight components that are able to be more feasibly transported within a vehicle used by medical personnel (e.g., a doctor, veterinarian, medical technician, nurse, etc.). Additionally, and as will be explained in greater detail, the system 1000 enables the isolation of α2M molecules for injection into a joint or other musculoskeletal structure in less time than is possible in the prior art. For sake of clarity, it should be noted that the one or more isolators 700 depicted and discussed in the present application were each earlier referred to as a "centrifugal concentrator" in the aforementioned U.S. Provisional Application 63/209,685 filed Jun. 11, 2021, the disclosure of which is incorporated herein by reference for all purposes.

Still referring to FIG. 1, the isolation of α2M molecules for use in treating a musculoskeletal condition begins with use of the whole blood syringe 200 to draw an amount of whole blood from the patient to be treated (regardless of whether the patient is a human being or other form of animal), and then convey portions of that blood into each of multiple separator tubes 300. The set of separator tubes 300 may then be placed within the centrifuge 500 to be subjected to centrifugal force for a first predetermined period of time (i.e., a first stage of centrifuging) to cause separation of the blood plasma containing the α2M molecules from other components of the whole blood with the aid of a separator gel incorporated into each of the separator tubes 300. Following such separation of the plasma from the other blood components, one or both of a transfer device 400 and a transfer syringe 600 may then be used to retrieve the separated blood plasma from each of the separator tubes 300, and transfer that plasma to one or more isolators 700. The one or more isolators 700 may then be placed within the centrifuge 500 to be subjected to centrifugal force for a second predetermined period of time (i.e., a second stage of centrifuging) to cause isolation of the α2M molecules from the plasma with the aid of a membrane filter incorporated into each isolator 700. Following such isolation of the α2M molecules, the injectate syringe 800 may then be used to retrieve the α2M molecules from the one or more isolators 700 in preparation for injecting the now isolated α2M molecules into a joint or other musculoskeletal structure of the patient.

Turning to FIG. 2A, as depicted, the set of separator tubes 300 may be either a set of non-vacuum separator tubes 300a or a set of vacuum separator tubes 300b. Each of the different types of separator tube 300a and 300b may be an elongate transparent tube with a single opening on one end that is sealed with a cap 310 to at least maintain sterile conditions therein. The cap 310 may be formed from a relatively flexible material that enables a hollow needle to penetrate therethrough for transferring gases and/or fluids into and/or out of the interior of each of the separator tubes 300a or 300b in a manner in which a seal is maintained around such a needle. Such a flexible material may also be self-sealing in a manner that causes a re-sealing of holes formed therethrough by the penetration and subsequent removal of such a needle.

In embodiments of the system 1000 that include the set of vacuum separator tubes 300b, each of the vacuum separator tubes 300b may be a VACUTAINER® tube of a type offered by Becton, Dickson and Company of Franklin Lakes, New Jersey, USA. As will be familiar to those skilled in the art, each such vacuum separator tube 300b, in its new and unused condition, may be pre-provided with a vacuum therein that the seal provided by the cap 310 is used to maintain.

Regardless of which of the separator tubes 300a or 300b are used, the quantity of separator tubes 300a or 300b that are used may vary based on such factors as the volume of whole blood 110 that may be safely drawn from the patient, the type and/or severity of the musculoskeletal condition that is to be treated, and/or the maximum quantity of separator tubes 300a or 300b that may be used with the centrifuge 500 at a time. Thus, it is contemplated that the system 1000 may be offered in differently-sized variants of kits, such as a smaller variant of kit that may include 1 to 4 separator tubes 300a or 300b, a mid-sized variant of kit that may include 5 to 8 separator tubes 300a or 300b, and/or a larger variant of kit that may include 9 to 16 (or still more) separator tubes 300a or 300b.

A plunger 220 of the whole blood syringe 200 may be operated to draw whole blood 110 from a blood vessel of a patient (whether a human being or other form of animal) and into the whole blood syringe 200 via a needle 211 thereof. The whole blood syringe 200 may include a human-readable scale by which the volume of whole blood that is drawn is able to be measured as the plunger 220 is so operated to ensure that just the amount of whole blood 110 that is needed for the chosen quantity of separator tubes 300a or 300b is successfully drawn. After the appropriate volume of whole blood 110 is drawn, the whole blood syringe 200 may then be used to inject a portion of the drawn whole blood into each of the separator tubes 300a or 300b through the cap 310 via the needle 211.

As additionally depicted, in some embodiments, and prior to being used to draw whole blood 110 from the patient, the whole blood syringe 200 may be partially pre-filled (e.g., by the nurse, medical technician, veterinarian technician, doctor, veterinarian, etc.) with an amount of an anticoagulant 250, such as a citrate dextrose solution (ACD-A), to prevent the drawn whole blood from coagulating therein.

Turning to FIG. 2B, each of the different types of separator tube 300a and 300b may include (at least in its new and unused condition) a small amount of a separator gel 350 disposed toward the end opposite the end that is closed with the cap 310. Thus, as depicted, following the collection and storage of the whole blood 110 among the set of separator tubes 300a or 300b, as described above in reference to FIG. 2A, the portion of the whole blood 110 within each of the separator tubes 300a or 300b may be disposed therein between the cap 310 at one end and the separator gel 350 at the other end.

With the set of separator tubes 300a or 300b so filled with portions of whole blood 110, the set of separator tubes 300a or 300b may be placed within the centrifuge 500 to be subjected to centrifugal force for a first period of time that is deemed sufficient to fully separate the plasma 113 thereof from the red and white blood cells 111 thereof. More specifically, and as depicted, the centrifuge 500 may be used in conjunction with the separator gel 350 to effect such a separation of components of the whole blood 110. Thus, when such isolation of the plasma 113 is complete, the separator gel 350 within each of the separator tubes 300a or 300b should occupy a position that physically separates the plasma 113 from the red and white blood cells 111, thereby preventing these blood components 111 and 113 from becoming mixed together, again.

As depicted, and as will be familiar to those skilled in the art, the centrifuge 500 may include a rotor 553 that defines a set of holding positions 530 that each have a shape and dimensions selected to hold a tube of matching shape and dimensions, such as one of the separator tubes 300a or 300b. As also depicted, it may be that the quantity and placement of such holding positions 530, as defined by the rotor 553, may be selected to enable various quantities of such tubes to be distributed among the holding positions 530 in a manner that distributes the weight thereof in a balanced manner that enables relatively smooth operation of the centrifuge 500.

As will also be familiar to those skilled in the art, it may be that the depicted rotor 553 is exchangeable within one or more other rotors to thereby enable the centrifuge to reconfigured to work with various different quantities and/or combinations of various tubes and/or other varieties of containers of differing shapes and/or sizes. Alternatively or additionally, it may be that the centrifuge 500 is fitted with (or otherwise includes) a rotor with 2 or more "buckets." Each such bucket may be able to be fitted with any of a variety of differing types of holder that may each be designed to provide holding position(s) for a differing quantity of and/or combination of various tubes and/or other varieties of containers of differing shapes and/or sizes.

Figure 2C:
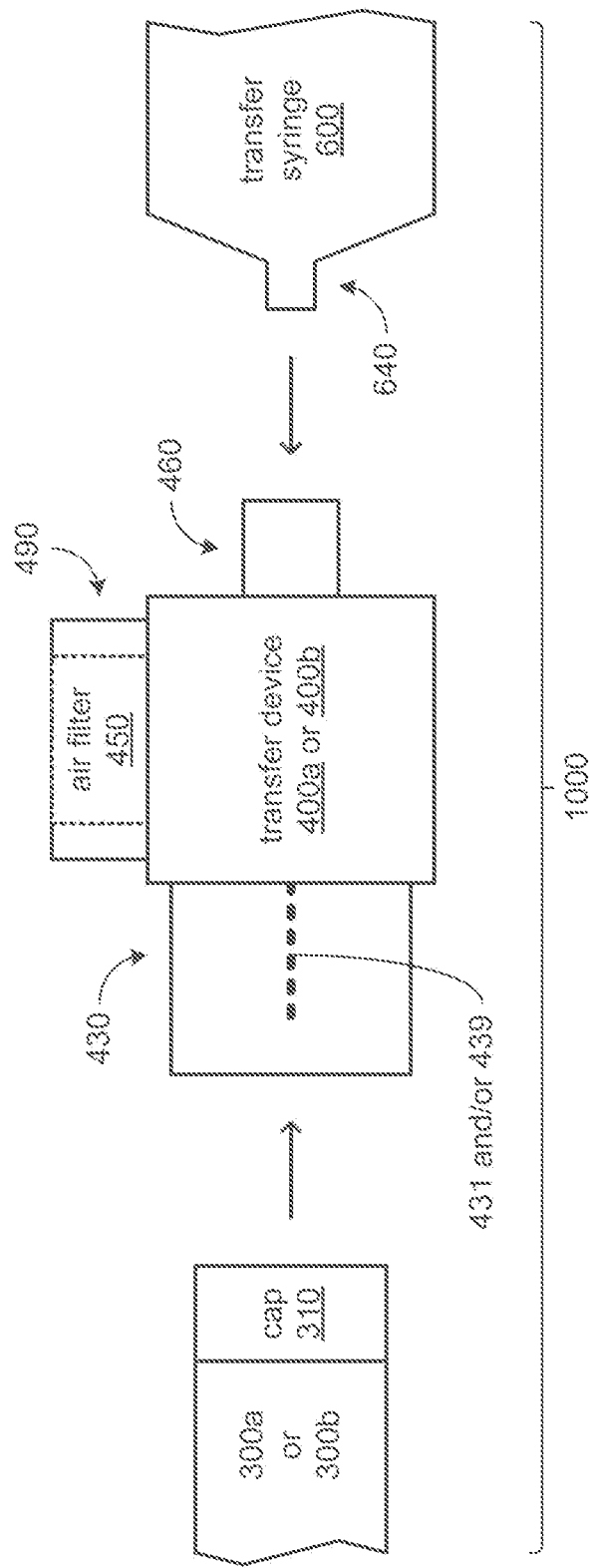

Turning to FIG. 2C, as depicted, in some embodiments of the system 1000, the transfer device 400 may be a dual-flow device 400a. Alternatively, in other embodiments of the system 1000, the transfer device 400 may be a three-way valve 400b.

Each of the different types of transfer device 400a and 400b may incorporate the depicted combination of a connected a separator tube port 430, a syringe port 460, and a filtered air port 490. As is about to be described, each of the different types of transfer device 400a and 400b is configured to configured to enable external air 990 surrounding the transfer device 400a or 400b to be drawn in through the air filter 450 at the filtered air port 490 and conveyed to a separator tube 300a or 300b coupled to the separator tube port 430 as part enabling plasma 113 to be transferred from the separator tube 300a or 300b to the transfer syringe 600 coupled to the syringe port 460.

It is envisioned that the interior volume of the transfer syringe 600 is sufficiently large that all of the sum total of the amounts of the plasma 113 isolated within all of the separator tubes 300a or 300b (as a result of being subjected to centrifugal force by the centrifuge 500) is able to be combined and retained within the transfer syringe 600. As a result, it is envisioned that the transfer syringe 600 is to remain connected to the syringe port 460 by its end connector 610 throughout the time that the plasma 113 is being transferred from each of the vacuum containers 100, and into the transfer syringe 600.

Figure 2D:
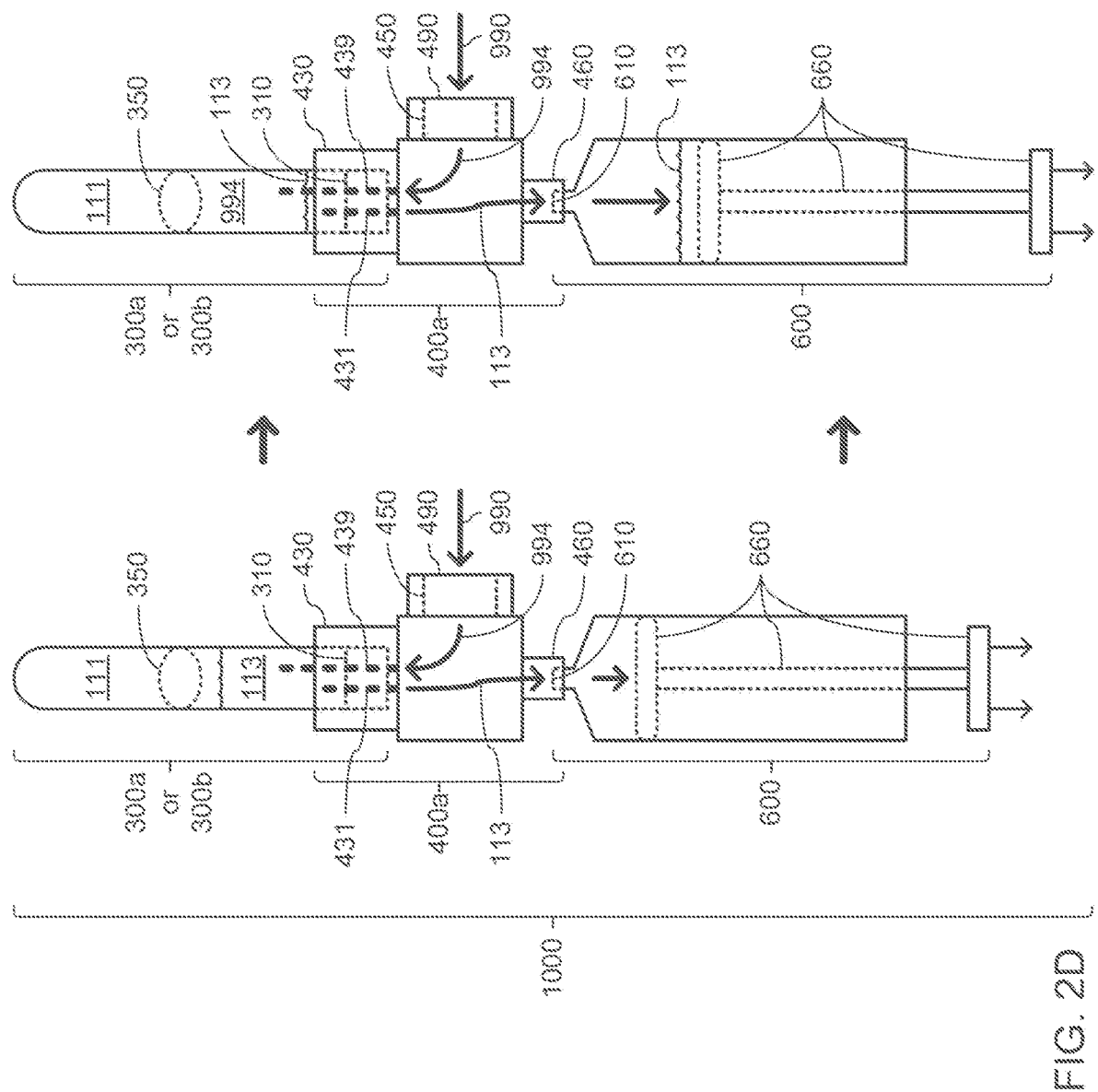

FIG. 2D depicts aspects of the manner in which the dual-flow device 400a enables a simultaneous transfer of filtered air 994 into a separator container 300a or 300b, and of plasma 113 out of the separator container 300a or 300b as part of transferring plasma 994 to the transfer syringe 600. As depicted, the separator tube port 430 may incorporate both an air needle 439 and a plasma needle 431 that are each positioned to penetrate through the cap 310 of a separator tube 300a or 300b to enable the flow through each of gases and/or liquids into and/or out of such a separator tube 300a or 300b. As also depicted, the syringe port 460 may be configured to form a connection with an end connector 610 carried at one end of the transfer syringe 600.

As depicted, with a separator tube 300a or 300b coupled to the separator tube port 430 such that the needles 431 and 439 penetrate the cap 310 thereof, and with the end connector 610 of the transfer syringe 600 coupled to the syringe port 460, there may be an initial equalization of pressures thereamong. More specifically, and especially where a vacuum separator tube 300b coupled to the separator tube port 430, external air 990 may be drawn into the dual-flow device 400a through the filtered air port 490, and conveyed into a separator tube 300a or 300b at the separator tube port 430 via the air needle 439. Pulling the plunger 660 of the transfer syringe 600 away from the end connector 610 thereof may then draw plasma 994 from within the separator tube 300a or 300b, and into the transfer syringe 660, via the plasma needle 431 and the end connector 610. In turn, more filtered air 994 may be drawn into the separator tube 300a or 300b to replace the plasma 994 that is so drawn out.

Figure 2E:
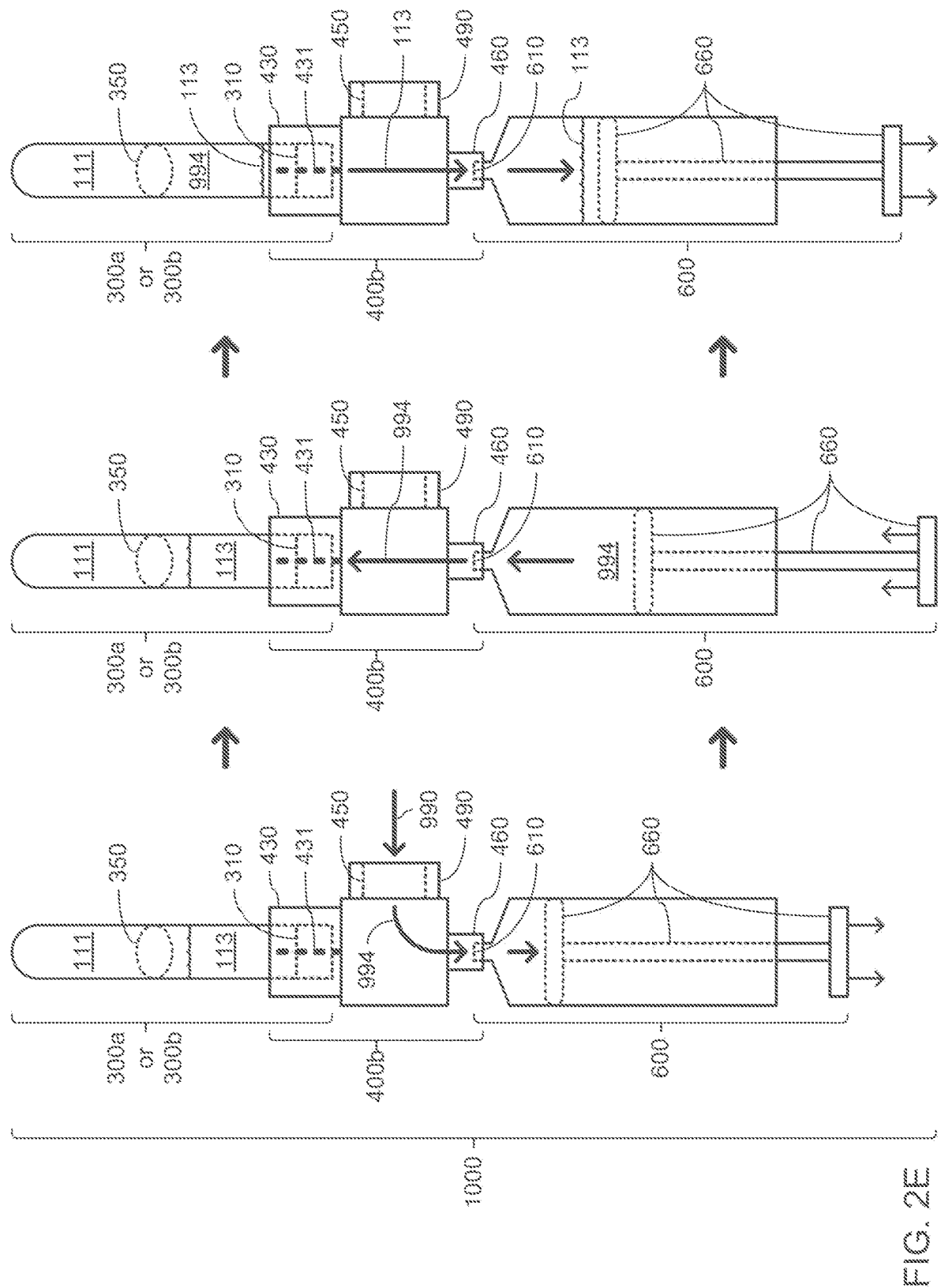

FIG. 2E depicts aspects of the manner in which the three-way valve 400b enables a selective transfer of filtered air 994 into a separator container 300a or 300b, and of plasma 113 out of the separator container 300a or 300b as part of transferring plasma 994 to the transfer syringe 600. As depicted, and unlike the dual-flow device 400a, the separator tube port 430 of the three-way valve 400b may incorporate just a single needle 431 that is positioned to penetrate through the cap 310 of a separator tube 300a or 300b to enable the flow therethrough of gases and/or liquids into and/or out of such a separator tube 300a or 300b. As also depicted, and similar to the dual-flow device 400a, the syringe port 460 may be configured to form a connection with an end connector 610 carried at one end of the transfer syringe 600.

Also unlike the dual-flow device 400a, the three-way valve 400b may incorporate a manually-operable valve (not specifically shown) of a type that is operable between at least two positions, where each position of the at least two positions causes one of the three ports 430, 460 or 490 to be closed off from the other two of these two ports, while allowing gases and/or liquids to flow freely between the other two.

As depicted, for each separator tube 300a or 300b that is connected to the separator tube port 430, the transfer of plasma 113 therefrom, and into the transfer syringe 600, may begin with the three-way valve 400b being operated to close off the separator tube port 430, thereby connecting the syringe port 460 to the filtered air port 490. With the separator tube port 430 so closed off, the plunger 660 of the transfer syringe 600 may be operated to draw filtered air 994 into the transfer syringe 600. More precisely, the plunger 660 of the transfer syringe 600 may be operated to cause external air 990 that surrounds the three-way valve 400b to be drawn in through the air filter 450, thereby being filtered to become the filtered air 994 that is drawn into the transfer syringe 600.

With an amount of such filtered air 994 now within the transfer syringe 600, the three-way valve 400b may then operated to close off the filtered air port 490, thereby connecting the syringe port 460 to the separator tube port 430. With the filtered air port 490 so closed off, the plunger 660 of the transfer syringe 600 may be operated to send filtered air 994 out of the transfer syringe 600, through the three-way valve 400b, through the single needle 431, and into the separator tube 300a or 300b that is coupled to the separator tube port 430. With filtered air 994 so conveyed into the separator tube 300a or 300b, the plunger 660 of the transfer syringe 600 may then be operated to draw most, if not all, of the plasma 113 out of the separator tube 300a or 300b, through the single needle 431, through the three-way valve 400b, and into transfer syringe 600.

Referring back to both FIGS. 2D and 2E, it should be noted, that such transfers of plasma 113 from the separation tubes 300a or 300b, and into the transfer syringe 600 may need to be performed with the depicted combination of the separation tube 300a or 300b, the transfer device 400a or 400b, and the transfer syringe 600 held in an orientation in which the separation tube 300a or 300b is at a higher elevation than the transfer syringe 600.

Figure 2F:
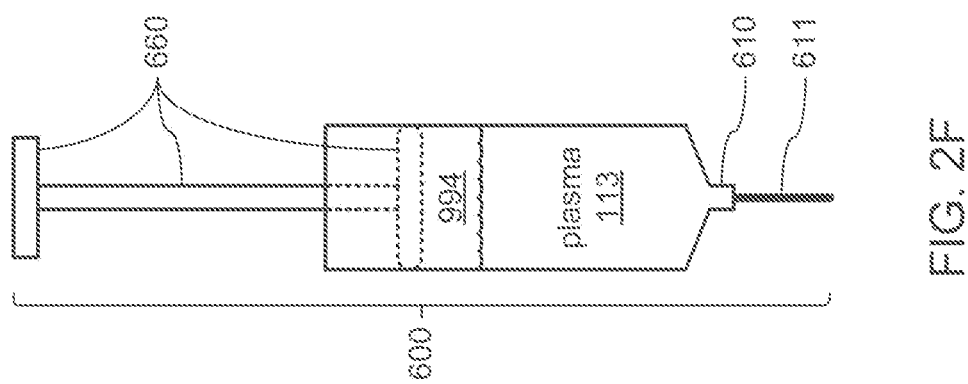

Turning FIG. 2F, following the transfer of plasma 113 out of each of the separation tubes 300a or 300b, and into the transfer syringe 600, the transfer syringe 600 may then be disconnected from the transfer device 400a or 400b. Then, a needle 611 may be connected to the end connector 610 of the transfer syringe 600 in preparation for injecting the plasma 113 into the isolator 700.

Turning to FIG. 2G, as depicted, the isolator 700 may include a combination of a first cylinder 701 and a second cylinder 702. Both of these cylinders 701 and 702 may be of a generally elongate shape defining a pair of ends.

One end of the first cylinder 701 may be sealed (or sealable) with a septum cap 710 that may provide a self-sealing aperture through which a needle or other form of tube of relatively small diameter tube may be inserted to effect the transfer of gases and/or liquids into and/or out of the interior volume of the first cylinder 701. The other end of the first cylinder 701 may incorporate a membrane filter 750. In some embodiments, the membrane filter 750 may have a filter diameter ranging from 100 kD to 500 kD.

The second cylinder 702 may be configured to make the isolator 700 more amenable for use with the centrifuge 700. More specifically, one end of the second cylinder 702 may be closed off with a conical end to ease insertion into the centrifuge 500, while the other end may be open to enable the two cylinders 701 and 702 to be assembled by inserting part of the end of the first cylinder 701 that includes the membrane filter 750 therein.

It should be noted, and as depicted, in some embodiments, the isolator 700 may be of an extended length variation 700a in which the volume of the first cylinder 701 is increased by sealing the end opposite the membrane filter 750 with an extended variant of the septum cap 710 that provides a cylindrical extension to the cylindrical wall of the first cylinder 701 to increase the length of the first cylinder 701. Alternatively, in other embodiments, the isolator 700 may be of a standard length variation 700b in which the volume of the first cylinder 701 is not so increased. More precisely, instead of sealing the end opposite the membrane filter 750 with the extended variant of the septum cap 710, a standard variant of the septum cap 710 is used that does not provide the cylindrical extension.

Figure 2H:
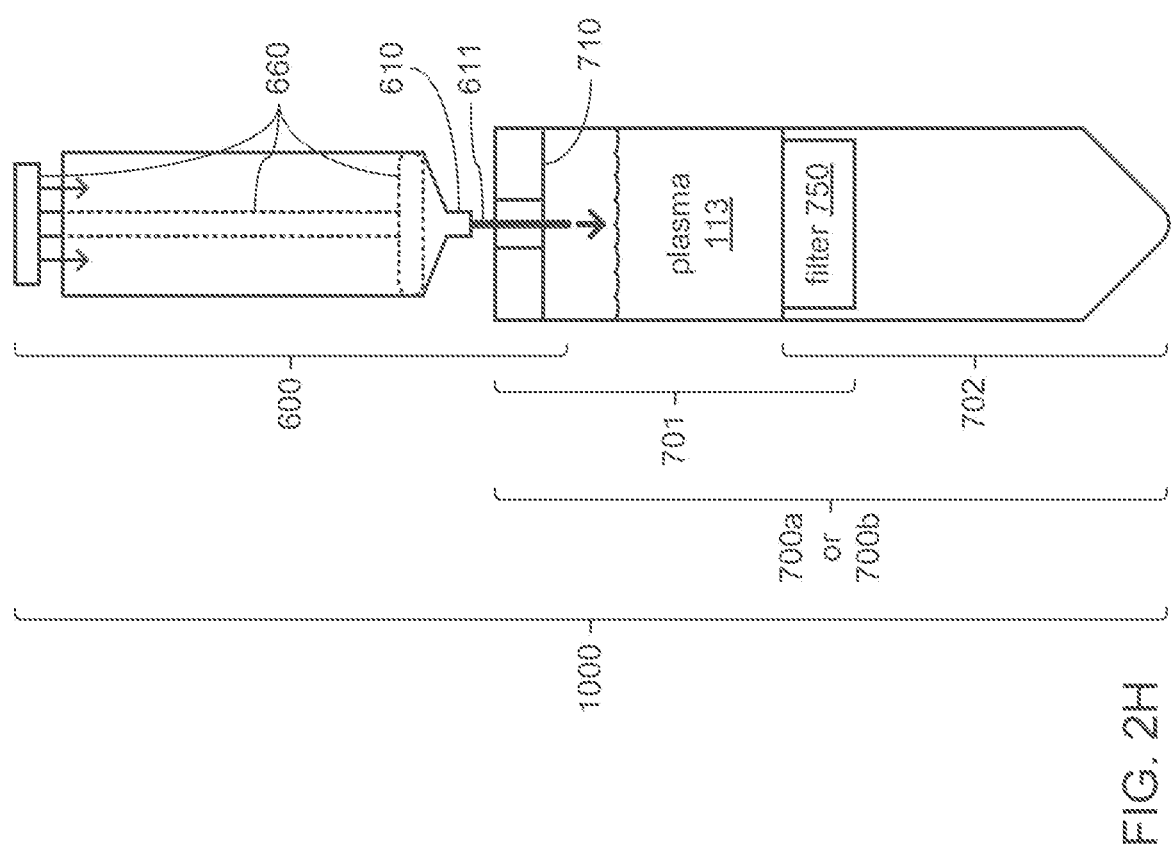

Turning to FIG. 2H, with the isolator 700a or 700b assembled, and with the needle 611 connected to end connector 610 of the transfer syringe 600, the needle 611 may then be inserted through the aperture of the septum cap 710. The plunger 660 of the transfer syringe 600 may then be operated to transfer the plasma 113 out of the transfer syringe 600, and into the first cylinder 701 through the needle 611 and the aperture of the septum cap 710.

Figure 2I:
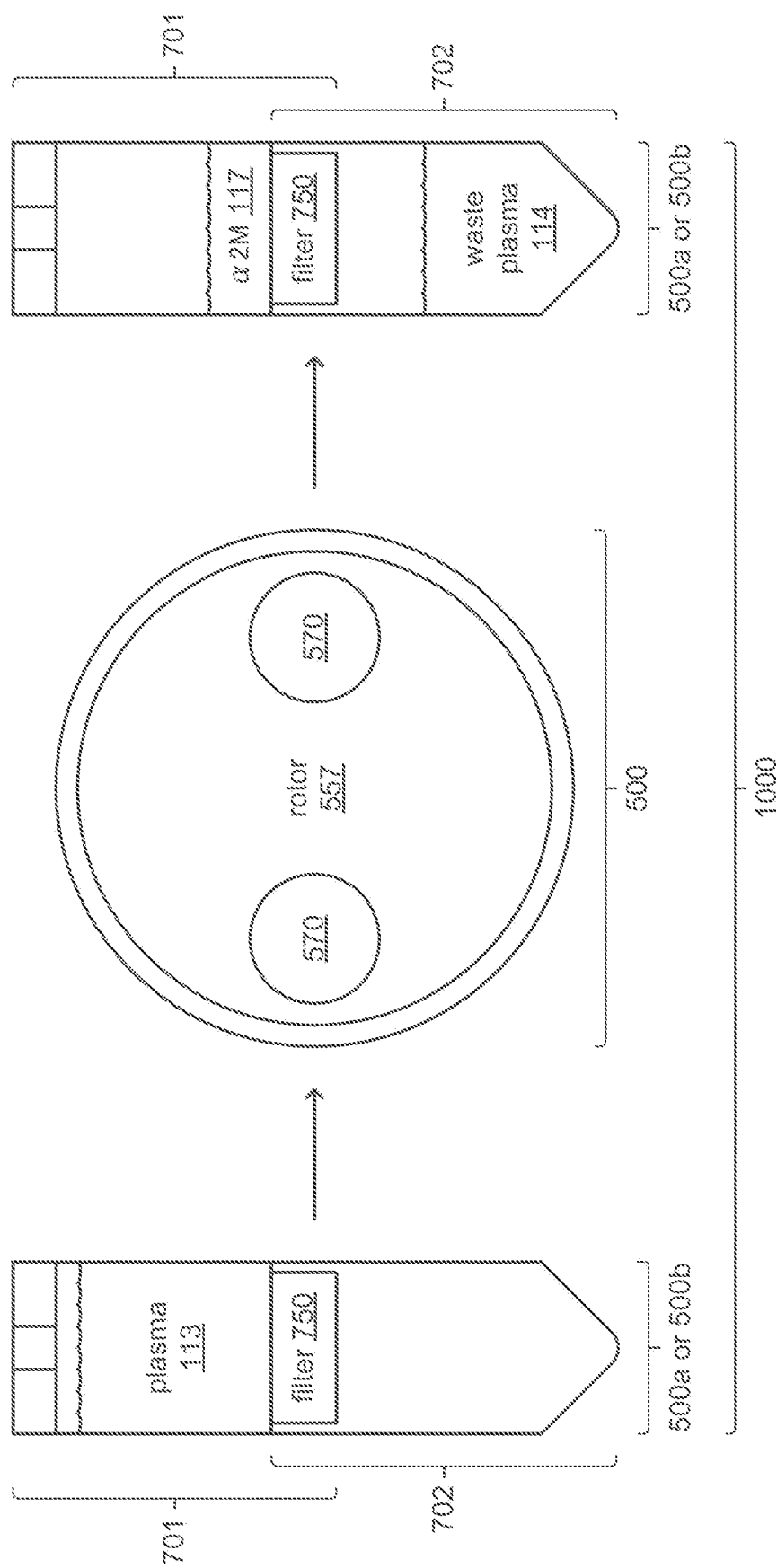

Turning to FIG. 2I, after the plasma 113 has been transferred into the first cylinder 701, the still assembled isolator 700 may be placed within the centrifuge 500 to be subjected to centrifugal force for a second period of time that is deemed sufficient to fully separate the α2M molecules 117 from the rest of the plasma 113 originally transferred into the first cylinder 701. More specifically, and as depicted, the centrifuge 500 may be used in conjunction with the membrane filter 750 to effect such a separation of components of the plasma 113. Thus, when such isolation of the α2M molecules 117 is complete, the α2M molecules 117 should remain within the first cylinder 701, while the other components of the plasma 114 should be retained within the second cylinder 702 as the depicted waste plasma 114.

In a manner similar to what was discussed in reference to FIG. 2B, the centrifuge 500 may include a rotor 557 that defines a pair of holding positions 570 that each have a shape and dimensions selected to hold a tube of matching shape and dimensions, such as the isolator 700. As also depicted, it may be that the pair of such holding positions 570, as defined by the rotor 557, may be positioned to enable the placement of a pair of the isolators 700 at locations that distribute the weight thereof in a balanced manner that enables relatively smooth operation of the centrifuge 500.

Further, and as also previously discussed, there may be various variants of the system 1000 offered to provide a range of capacities, such as the aforedescribed smaller, mid-size and larger variants with different quantities of separator tubes 300a or 300b. It should be noted that, correspondingly, such a range of variants may also include differing quantities of isolators 700. More specifically, and by way of example, it may be that the aforedescribed smaller and mid-sized variants include a single isolator 700, while the larger variant includes two of the isolators 700. In such variants that include just a single isolator 700, a dummy weight of a shape and size similar to the isolator 700 may be included to provide a counterbalance to the weight of the isolator 700 with plasma 113 therein to enable balancing of the centrifuge 500.

However, as an alternative to providing a dummy weight, it may be that all of the aforedescribed size variants of the system 1000 may be provided with a pair of isolators 700. It may be that, for the aforedescribed smaller and mid-sized variants, the second one of the two isolators 700 is to be filled with water to serve the purpose of being the counterbalance.

As will also be familiar to those skilled in the art, it may be that the depicted rotor 553 is exchangeable within one or more other rotors to thereby enable the centrifuge to reconfigured to work with various different quantities and/or combinations of various tubes and/or other varieties of containers of differing shapes and/or sizes. Alternatively or additionally, it may be that the centrifuge 500 is fitted with (or otherwise includes) a rotor with 2 or more "buckets." Each such bucket may be able to be fitted with any of a variety of differing types of holder that may each be designed to provide holding position(s) for a differing quantity of and/or combination of various tubes and/or other varieties of containers of differing shapes and/or sizes.

It should be noted that such use of the isolator 700 with the centrifuge 500 to perform the separation of the α2M molecules 117 from the rest of the plasma 113 originally transferred into the first cylinder 701 has been found to be faster than the prior art use of a peristaltic pump. The centrifuge 500 is also a far simpler, more durable and far less expensive piece of equipment than a peristaltic pump such that equipping a vehicle used to make house calls with the centrifuge 500 is far more feasible.

Figure 2J:
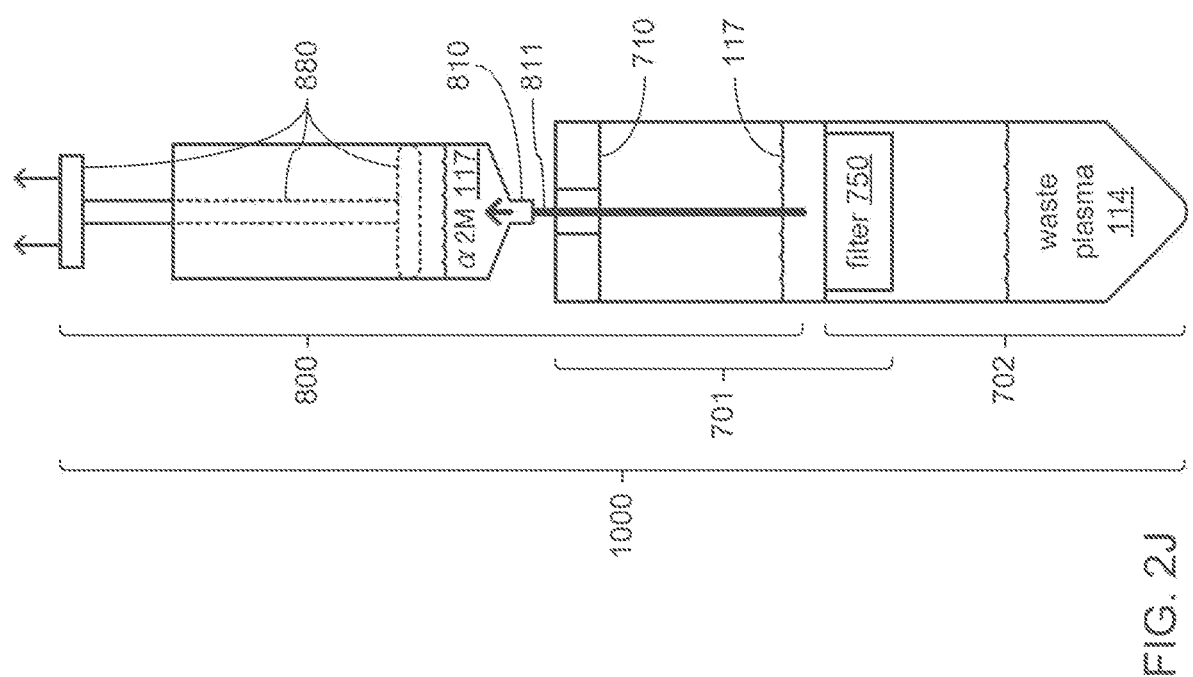

Turning to FIG. 2J, following such isolation of the α2M molecules 117, a needle 811 connected to an end connector 810 of an injectate syringe 800 may be inserted through the aperture of the septum cap 710. With the needle 811 so inserted, a plunger 880 of the injectate syringe 800 may then be operated to transfer the α2M molecules 117 from the first cylinder 701, and into the injectate syringe 800. Where more than one isolator 700 is used to isolate the α2M molecules 117 of a particular patient, such operations may be repeated to transfer the α2M molecules 117 out of each such isolator 700.

In some embodiments, with the most (if not all) of the α2M molecules 117 so transferred into the injectate syringe 800, the injectate syringe 800 may then be used directly to inject the α2M molecules 117 into a joint or other musculoskeletal structure of the patient. Alternatively, the injectate syringe 800 may be used to transfer the α2M molecules 117 into one or more other syringes (not shown) that may then be used to inject the α2M molecules 117 into a joint or other musculoskeletal structure of the patient. As still another alternatively, the injectate syringe 800 may be used to transfer the α2M molecules 117 into storage vials or still other container(s) (not shown) for temporary storage in preparation for the α2M molecules 117 to be so injected into a joint or other musculoskeletal structure of the patient at a later time.

FIG. 3 is a flowchart 2100 depicting aspects of the operation of an α2M molecule isolation system to perform a method of isolating α2M molecules from a patient's whole blood for use in treating a musculoskeletal condition of that patient.

At 2110, whole blood may be drawn from a patient (e.g., a human being or other form of animal) who/that may be suffering from a musculoskeletal condition affecting a joint or other musculoskeletal structure. As has been discussed, a syringe inserted into an artery or vein of the patient may be used (e.g., the whole blood syringe 200 of the system 1000).

At 2112, the whole blood may be transferred to one or more separator tubes that may each be preloaded with a separator gel (e.g., one or more of the separator tubes 300a or 300b that are each preloaded with an amount of the separator gel 350). As has been discussed, depending on such factors as the species of the patient, the type and/or severity of the condition to be treated, and/or still other factors, the quantity of separator tubes may vary. Again, there may be more than one variant of the system that may be differentiated by the quantity of separator tubes that it may include.

At 2120, the separator tube(s) may be placed within a centrifuge (e.g., the centrifuge 500), and the centrifuge may be operated to exert centrifugal force on the separator tube(s) in a first stage of centrifuging. In this way, a combination of the exerted centrifugal force and the separator gel within each separator tube may be used to separate the plasma of the whole blood from at least the red and white blood cells of the whole blood.

At 2130, at least a transfer syringe (e.g., the transfer syringe 600) may be used to retrieve the plasma from within the separator tube(s), and to transfer the plasma into at least one isolator incorporating a filter (e.g., at least one of the isolator 700 incorporating the filter 750). As has been discussed, just as the quantity of separator tubes may vary across multiple variations of the system, it may be that the quantity of isolators also varies in a manner that is at least partially correlated to the quantity of separator tubes. Alternatively, it may be that a pair of isolators is regularly included with the expectation that, where they are not both used, the unused one may be filled with an amount of water or other substance to serve as a counterbalance to the one that is used during a second stage of centrifuging.

At 2140, the isolator(s) may be placed within the centrifuge, and the centrifuge may be operated to exert centrifugal force on the isolator(s) in the aforementioned second stage of centrifuging. In this way, a combination of the exerted centrifugal force and the filter within each isolator that is filled with plasma may be used to isolate the α2M molecules from other components of the plasma. Again, where just one isolator is filled with plasma, a counterbalancing weight, or other isolator that is filled with water or another substance to serve as a counterbalancing weight, may be required to balance the centrifuge.

At 2150, an injectate syringe (e.g., the injectate syringe 800) may be used to retrieve the α2M molecules from within the isolator(s).

At 2160, the patient may then be treated with the α2M molecules, either with injection(s) directly from the injectate syringe, or from other syringe(s) to which the α2M molecules may be transferred from the injectate syringe. Alternatively, at 2160, the α2M molecules may be stored for later use in such treatment.

There is thus disclosed an α2M molecule isolation system and method for isolating of α2M molecules from whole blood of a patient in preparation for use in treating a musculoskeletal condition of that patient.

A method for isolating Alpha-2 Macroglobulin (α2M) molecules from whole blood includes: depositing whole blood into at least one separator tube, wherein each separator tube of the at least one separator tube contains an amount of separator gel; subjecting the at least one separator tube to a first centrifugal force in a first centrifuging stage for a first predetermined period of time to cause a combination of the first centrifugal force and the separator gel within each separator tube of the at least one separator tube to separate plasma of the whole blood within the at least one separator tube from red blood cells and white blood cells of the whole blood within the at least one separator tube, wherein the plasma includes the α2M molecules; transferring one or more portions of the plasma from within the at least one separator tube and into at least one isolator, wherein each isolator of the at least one isolator comprises a filter; and subjecting the at least one isolator to a second centrifugal force in a second centrifuging stage for a second predetermined period of time to cause a combination of the second centrifugal force and the filter within each isolator of the at least one isolator to isolate the α2M molecules from other components of the plasma within the at least one isolator.

The method may further include: retrieving at least a portion of the α2M molecules from within the at least one isolator; and injecting at least the portion of the α2M molecules into a musculoskeletal structure of a patient from which the whole blood was drawn.

Each separator tube of the at least one separator tube may include an elongate transparent tube that defines an opening at one end that is sealed with a cap, and the cap may be formed from a flexible material that allows a hollow needle of a syringe to penetrate therethrough while sealing around the hollow needle, and that re-seals after the hollow needle is withdrawn. Depositing the whole blood into at least one separator tube may include: inserting a needle of the syringe through the cap of each separator tube of the at least one separator tube; and injecting at least a portion of the whole blood into each separator tube of the at least one separator tube from within the syringe.

Each separator tube of the at least one separator tube may include either a non-vacuum separator tube, or a vacuum separator tube that is pre-provided with a vacuum therein when in an unused condition.

The method may further include: using the syringe to draw the whole blood from a patient into which the α2M molecules are to be injected; and partially pre-filling the syringe with an anticoagulant before using the syringe to draw the whole blood from the patient.

Subjecting the at least one separator tube to the first centrifugal force in the first centrifuging stage may include placing the at least one separator tube within a first holder of a centrifuge, and operating the centrifuge to exert the first centrifugal force on the at least one separator tube; subjecting the at least one isolator to the second centrifugal force in the second centrifuging stage may include placing the at least one isolator within a second holder of the centrifuge, and operating the centrifuge to exert the second centrifugal force on the at least one isolator; the first holder may include either a first removable holder configured to be inserted into a bucket of the centrifuge, or a first exchangeable rotor of the centrifuge; and the second holder may include either a second removable holder configured to be inserted into a bucket of the centrifuge, or a second exchangeable rotor of the centrifuge.

Transferring the one or more portions of the plasma from within the at least one separator tube and into the at least one isolator may include: using a transfer syringe to withdraw the one or more portions of the plasma from within the at least one separator tube; and using the transfer syringe to deposit the one or more portions of the plasma into the at least one isolator.

The at least one separator tube, the centrifuge, the transfer syringe and the at least one isolator, together, may form a kit for isolating the α2M molecules from the whole blood; and multiple versions of the kit may be defined by at least one of a quantity of separator tubes included in the at least one separator tube and a quantity of isolators included in the at least one isolator.

Transferring the one or more portions of the plasma from within the at least one separator tube and into the at least one isolator may further include: coupling the transfer syringe to a syringe port of a transfer device; coupling each separator tube of the at least one separator tube, one at a time, to a separator tube port of the transfer device, wherein the separator tube port comprises at least one hollow needle configured to simultaneously couple the separator tube port to the syringe port and to a filtered air port of the transfer device; and while each separator tube of the at least one separator tube is coupled to the separator tube port, operating a plunger of the transfer syringe to withdraw at least one portion of the one or more portions of the plasma from the separator tube and into the transfer syringe through the transfer device, and to simultaneously cause air to be drawn through an air filter at the filtered air port and into the separator tube through the transfer device.

Transferring the one or more portions of the plasma from within the at least one separator tube and into the at least one isolator may further include coupling the transfer syringe to a syringe port of a three-way valve, coupling each separator tube of the at least one separator tube, one at a time, to a separator tube port of the three-way valve, and while each separator tube of the at least one separator tube is coupled to the separator tube port, performing operations including: with the three-way valve operated to couple a filtered air port of the three-way valve to the syringe port, operating a plunger of the transfer syringe to draw air through an air filter at the filtered air port, through the three-way valve, and into the transfer syringe; and with the three-way valve operated to couple the separator tube port to the syringe port, operating the plunger of the transfer syringe to inject the filtered air into the separator tube through the three-way valve, and to withdraw at least one of the one or more portions of the plasma from the separator tube and into the transfer syringe through the three-way valve.

Each isolator of the at least one isolator may include a first cylinder defined by a first cylindrical wall and a second cylinder defined by a second cylindrical wall; a first end of the first cylindrical wall of the first cylinder may define an opening that is configured to be closable with a septum cap, and a second end of the first cylindrical wall is closed with the filter; a first end of the second cylindrical wall of the second cylinder may be closed where the second cylindrical wall narrows to form a conically-shaped end portion, and the second end of the second cylindrical wall of the second cylinder defines an opening that is configured to be coupled to the second end of the first cylinder in a manner that causes a first interior space of the first cylinder and a second interior space of the second cylinder to be separated by the filter; and at least a portion of the septum cap may be formed from a flexible material that allows a hollow needle of a syringe to penetrate therethrough while sealing around the hollow needle, and that re-seals after the hollow needle is withdrawn. Transferring the one or more portions of the plasma from within the at least one separator tube and into the at least one isolator may further include: using a transfer syringe to withdraw the one or more portions of the plasma from within the at least one separator tube; inserting a needle of the transfer syringe through the septum cap of each isolator of the at least one isolator; and injecting the one or more portions of the plasma into the first interior space from within the transfer syringe. Isolating the α2M molecules from other components of the plasma within the at least one isolator may include isolating the α2M molecules from other components within the first interior space of each isolator of the at least one isolator from the other components of the plasma within the second interior space of each isolator of the at least one isolator.

The septum cap may further include a third cylindrical wall configured to serve as an extension to the first cylindrical wall to increase a volume of the first interior space when the first end of the first cylindrical wall is closed with the septum cap.

A kit for isolating Alpha-2 Macroglobulin (α2M) molecules from whole blood includes at least one separator tube, wherein: each separator tube of the at least one separator tube comprises an elongate transparent tube that defines an opening at one end that is sealed with a cap; each separator tube of the at least one separator tube contains an amount of separator gel; the cap is formed from a flexible material that allows a hollow needle of a transfer syringe to penetrate therethrough while sealing around the hollow needle, and that re-seals after the hollow needle is withdrawn; and the kit is available in multiple versions that are differentiated by at least a quantity of separator tubes that are included. The kit also includes at least one isolator, wherein: each isolator of the at least one isolator comprises a first cylinder defined by a first cylindrical wall and a second cylinder defined by a second cylindrical wall; each isolator of the at least one isolator comprises a filter; a first end of the first cylindrical wall of the first cylinder defines an opening that is configured to be closable with a septum cap, and a second end of the first cylindrical wall is closed with the filter; a first end of the second cylindrical wall of the second cylinder is closed where the second cylindrical wall narrows to form a conically-shaped end portion, and the second end of the second cylindrical wall of the second cylinder defines an opening that is configured to be coupled to the second end of the first cylinder in a manner that causes a first interior space of the first cylinder and a second interior space of the second cylinder to be separated by the filter; and at least a portion of the septum cap is formed from a flexible material that allows the hollow needle of the transfer syringe to penetrate therethrough while sealing around the hollow needle, and that re-seals after the hollow needle is withdrawn. The kit further includes a centrifuge that is configured to: subject the at least one separator tube to a first centrifugal force in a first centrifuging stage for a first predetermined period of time to cause a combination of the first centrifugal force and the separator gel within each separator tube of the at least one separator tube to separate plasma of the whole blood within the at least one separator tube from red blood cells and white blood cells of the whole blood within the at least one separator tube, wherein the plasma includes the α2M molecules; and subject the at least one isolator to a second centrifugal force in a second centrifuging stage for a second predetermined period of time to cause a combination of the second centrifugal force and the filter within each isolator of the at least one isolator to isolate the α2M molecules from other components of the plasma within the at least one isolator. The additionally includes the transfer syringe, wherein, between the first centrifuging stage and the second centrifuging stage, the transfer syringe is configured to transfer the plasma from the at least one separator tube and into the at least one isolator by: being inserted through the cap of each separator tube of the at least one separator tube to withdraw the plasma from within the at least one separator tube; and being inserted through the septum cap of each isolator of the at least one isolator to inject the plasma into the at least one isolator.

Each separator tube of the at least one separator tube may include either a non-vacuum separator tube, or a vacuum separator tube that is pre-provided with a vacuum therein when in an unused condition.

The centrifuge may further include at least one exchangeable rotor to enable the centrifuge to be used in the first centrifuging stage and the second centrifuging stage by exchanging the at least one exchangeable rotor.

The centrifuge may further include a rotor that is configured to define multiple buckets into which exchangeable holders of differing configurations may be installed to enable the centrifuge to be used in the first centrifuging stage and the second centrifuging stage by exchanging holders within the multiple buckets.

The kit may further include a transfer device, wherein: the transfer device may include a syringe port, a filtered air port comprising an air filter, and a separator tube port that comprises at least one hollow needle to configured to simultaneously couple the separator tube port to the syringe port and to the filtered air port; and while each separator tube of the at least one separator tube is coupled to the separator tube port, a plunger of the transfer syringe may be able to be operated to withdraw at least a portion of the plasma from the separator tube and into the transfer syringe through the transfer device, and to simultaneously cause air to be drawn through the air filter at the filtered air port and into the separator tube through the transfer device.

The kit may further include a three-way valve, wherein: the three-way valve may include a syringe port, a filtered air port comprising an air filter, and a separator tube port that comprises at least one hollow needle to configured to simultaneously couple the separator tube port to the syringe port and to the filtered air port. While each separator tube of the at least one separator tube is coupled to the separator tube port, the three-way valve and a plunger of the transfer syringe may be able to be operated to perform operations including: with the three-way valve operated to couple a filtered air port of the three-way valve to the syringe port, the plunger of the transfer syringe is able to be operated to draw air through the air filter at the filtered air port, through the three-way valve, and into the transfer syringe; and with the three-way valve operated to couple the separator tube port to the syringe port, the plunger of the transfer syringe is able to be operated to inject the filtered air into the separator tube through the three-way valve, and to withdraw at least a portion of the plasma from the separator tube and into the transfer syringe through the three-way valve.

Injecting the plasma into the at least one isolator may include injecting at least a portion of the plasma into the first interior space within the first cylinder of each isolator of the at least one isolator; and isolating the α2M molecules from other components of the plasma within the at least one isolator may include isolating the α2M molecules from other components within the first interior space of each isolator of the at least one isolator from the other components of the plasma within the second interior space within each isolator of the at least one isolator.

The septum cap may further include a third cylindrical wall configured to serve as an extension to the first cylindrical wall to increase a volume of the first interior space when the first end of the first cylindrical wall is closed with the septum cap.

The invention claimed is:
1. A kit for isolating Alpha-2 Macroglobulin (α2M) molecules from whole blood comprising:
at least one separator tube, wherein:
each separator tube of the at least one separator tube comprises an elongate transparent tube that defines an opening at one end that is sealed with a cap;
each separator tube of the at least one separator tube contains an amount of separator gel; and
the cap is formed from a flexible material that allows a hollow needle of a transfer syringe to penetrate therethrough while sealing around the hollow needle, and that re-seals after the hollow needle is withdrawn;
at least one isolator, wherein:
each isolator of the at least one isolator comprises a first cylinder defined by a first cylindrical wall and a second cylinder defined by a second cylindrical wall;
each isolator of the at least one isolator comprises a filter and a septum cap;
a first end of the first cylindrical wall of the first cylinder defines an opening that is configured to be closable with the septum cap, and a second end of the first cylindrical wall is closed with the filter;
a first end of the second cylindrical wall of the second cylinder is closed where the second cylindrical wall narrows to form a conically-shaped end portion, and the second end of the second cylindrical wall of the second cylinder defines an opening that is configured to be coupled to the second end of the first cylinder in a manner that causes a first interior space of the first cylinder and a second interior space of the second cylinder to be separated by the filter;

the second end of the first cylindrical wall and the second end of the second cylindrical wall share a common exterior diameter;

the filter remains at a fixed location relative to the first cylinder and relative to the second cylinder when the second end of the second cylinder is coupled to the second end of the first cylinder; and at least a portion of the septum cap is formed from a flexible material that allows the hollow needle of the transfer syringe to penetrate therethrough while sealing around the hollow needle, and that re-seals after the hollow needle is withdrawn;

a centrifuge that is configured to:

subject the at least one separator tube to a first centrifugal force in a first centrifuging stage for a first predetermined period of time to cause a combination of the first centrifugal force and the separator gel within each separator tube of the at least one separator tube to separate plasma of the whole blood within the at least one separator tube from red blood cells and white blood cells of the whole blood within the at least one separator tube, wherein the plasma includes the α2M molecules; and subject the at least one isolator to a second centrifugal force in a second centrifuging stage for a second predetermined period of time to cause a combination of the second centrifugal force and the filter within each isolator of the at least one isolator to isolate the α2M molecules from other components of the plasma within the at least one isolator;

the transfer syringe, wherein, between the first centrifuging stage and the second centrifuging stage, the transfer syringe is configured to transfer the plasma from the at least one separator tube and into the at least one isolator through a transfer device; and the transfer device, comprising:

a separator tube port configured to receive each separator tube of the at least one separator tube;

a syringe port configured to receive an end connector of the transfer syringe, wherein the end connector is configured to be coupled to the hollow needle; and another hollow needle that couples the separator tube port to the syringe port to enable a portion of the plasma to be transferred from each separator tube of the at least one separator tube to the transfer syringe when a plunger of the transfer syringe is operated to withdraw the portion of the plasma from each separator tube of the at least one separator tube.

2. The kit of claim 1, wherein each separator tube of the at least one separator tube comprises either a nonvacuum separator tube, or a vacuum separator tube that is pre-provided with a vacuum therein when in an unused condition.

3. The kit of claim 1, wherein the centrifuge comprises at least one exchangeable rotor to enable the centrifuge to be used in the first centrifuging stage and the second centrifuging stage by exchanging the at least one exchangeable rotor.

4. The kit of claim 1, further comprising a first set of exchangeable holders and a second set of exchangeable holders, wherein the centrifuge comprises a rotor that is configured to define multiple buckets to enable the centrifuge to be used in the first centrifuging stage with the first set of exchangeable holders installed within the multiple buckets, and to enable the centrifuge to be used in the second centrifuging stage with the second set of exchangeable holders installed within the multiple buckets.

5. The kit of claim 1, wherein each isolator of the at least one isolator is configured to:

receive the injection of the plasma within the first interior space within the first cylinder; and isolate the α2M molecules within the first interior space from the other components of the plasma within the second interior space.

6. The kit of claim 5, wherein the septum cap further comprises a third cylindrical wall configured to serve as an extension to the first cylindrical wall to increase a volume of the first interior space when the first end of the first cylindrical wall is closed with the septum cap.

7. The kit for isolating Alpha-2 Macroglobulin (α2M) molecules from whole blood of claim 1, wherein the at least one separator tube is pre-provided with a vacuum therein that the seal provided by the cap is used to maintain.

8. The kit for isolating Alpha-2 Macroglobulin (α2M) molecules from whole blood of claim 1, wherein the transfer syringe includes a human-readable scale by which a volume of whole blood that is drawn is able to be measured as a plunger of the transfer syringe is operated to withdraw the whole blood.

9. The kit for isolating Alpha-2 Macroglobulin (α2M) molecules from whole blood of claim 1, wherein the transfer syringe includes a human-readable scale by which a volume of whole blood that is drawn is able to be measured as a plunger of the transfer syringe is operated to withdraw at least a portion of the plasma from the separator tube and into the transfer syringe through the transfer device.

10. The kit for isolating Alpha-2 Macroglobulin (α2M) molecules from whole blood of claim 1, further comprising a whole blood syringe and an amount of an anticoagulant carried within the whole blood syringe to prevent the drawn whole blood from coagulating therein.

11. The kit for isolating Alpha-2 Macroglobulin (α2M) molecules from whole blood of claim 10, wherein the anticoagulant comprises a citrate dextrose solution (ACD-A).

12. The kit for isolating Alpha-2 Macroglobulin (α2M) molecules from whole blood of claim 1, wherein the filter of each isolator of the at least one isolator has a molecular weight cut off ranging from 100 kD to 500 kD.

13. The kit for isolating Alpha-2 Macroglobulin (α2M) molecules from whole blood of claim 1, wherein the at least one separator tube comprises 1 to 4 separator tubes.

14. The kit for isolating Alpha-2 Macroglobulin (α2M) molecules from whole blood of claim 1, wherein the at least one separator tube comprises 5 to 8 separator tubes.

15. The kit for isolating Alpha-2 Macroglobulin (α2M) molecules from whole blood of claim 1, wherein the at least one separator tube comprises 9 to 16 separator tubes.

16. The kit for isolating Alpha-2 Macroglobulin (α2M) molecules from whole blood of claim 1, wherein the at least one separator tube comprises more than 16 separator tubes.

17. The kit for isolating Alpha-2 Macroglobulin (α2M) molecules from whole blood of claim 1, wherein:

the at least one isolator comprises just one isolator; and the kit further comprises a dummy isolator configured to cooperate with the centrifuge to provide a counterbalance to the just one isolator when subjecting the just one isolator during the second centrifuging stage.

* * * * *